United States Patent
Raptis et al.

(10) Patent No.: US 11,264,131 B2
(45) Date of Patent: Mar. 1, 2022

(54) SYSTEM AND METHOD FOR SAVING BATTERY POWER IN A PATIENT MONITORING SYSTEM

(71) Applicant: CAREFUSION 303, INC., San Diego, CA (US)

(72) Inventors: Mark Raptis, Valley Center, CA (US); Amir Jafri, San Diego, CA (US); Ganesh Kathiresan, Osterley (GB); Alison Burdett, Oxford (GB); Okundu Omeni, Hillingdon (GB); Mathew Key, Oxford (GB)

(73) Assignee: CAREFUSION 303, INC., San Diego, CA (US)

( * ) Notice: Subject to any disclaimer, the term of this patent is extended or adjusted under 35 U.S.C. 154(b) by 718 days.

(21) Appl. No.: 14/694,957

(22) Filed: Apr. 23, 2015

(65) Prior Publication Data
US 2015/0223706 A1    Aug. 13, 2015

Related U.S. Application Data

(62) Division of application No. 12/844,801, filed on Jul. 27, 2010, now Pat. No. 9,017,255.

(51) Int. Cl.
*G16H 40/67* (2018.01)
*H04W 52/02* (2009.01)
(Continued)

(52) U.S. Cl.
CPC ........... *G16H 40/67* (2018.01); *A61B 5/0002* (2013.01); *A61B 5/01* (2013.01); *A61B 5/02055* (2013.01);
(Continued)

(58) Field of Classification Search
CPC .................................................. Y10S 370/913
See application file for complete search history.

(56) References Cited

U.S. PATENT DOCUMENTS

| | | |
|---|---|---|
| 3,677,261 A | 7/1972 | Day |
| 3,805,769 A | 4/1974 | Sessions |

(Continued)

FOREIGN PATENT DOCUMENTS

| | | |
|---|---|---|
| EP | 1748289 A2 | 1/2007 |
| JP | 61003019 | 1/1986 |

(Continued)

OTHER PUBLICATIONS

Akyldiz, I.F. et al; "Wireless Multemedia Sensor Networks; A Survey". IEEE Wireless Communications. Dec. 2007, p. 32-39.
(Continued)

*Primary Examiner* — Lynsey C Eiseman
*Assistant Examiner* — Amanda L Steinberg
(74) *Attorney, Agent, or Firm* — Morgan, Lewis & Bockius LLP

(57) ABSTRACT

A vital-signs patch for a patient monitoring system is disclosed. The patch consists of a housing that is configured to be worn on the skin of a patient. The housing contains a radio, one or more sensor interfaces, a processor, and a battery. The processor can selectably turn portions of the processor off and on and selectably turn power off and on to at least a portion of the sensor interfaces and radio. The processor includes a timer that, each time the timer times out, will turn all the parts of the processor on and start a new timing period. When the processor receives a signal, the processor will turn off power to at least a portion of the processor and at least a portion of the sensor interfaces.

14 Claims, 7 Drawing Sheets

(51) Int. Cl.

| | | |
|---|---|---|
| *A61B 5/08* | (2006.01) | |
| *A61B 5/00* | (2006.01) | |
| *A61B 5/318* | (2021.01) | |
| *A61B 5/11* | (2006.01) | |
| *A61B 5/145* | (2006.01) | |
| *A61B 5/01* | (2006.01) | |
| *A61B 5/024* | (2006.01) | |
| *A61B 5/0205* | (2006.01) | |
| *A61B 5/1455* | (2006.01) | |

(52) U.S. Cl.
CPC ........ *A61B 5/02438* (2013.01); *A61B 5/0816* (2013.01); *A61B 5/318* (2021.01); *A61B 5/6823* (2013.01); *A61B 5/6833* (2013.01); *A61B 5/746* (2013.01); *H04W 52/0206* (2013.01); *H04W 52/0235* (2013.01); *H04W 52/0274* (2013.01); *A61B 5/002* (2013.01); *A61B 5/1116* (2013.01); *A61B 5/14542* (2013.01); *A61B 5/14551* (2013.01); *A61B 2560/0209* (2013.01); *A61B 2562/0219* (2013.01); *A61B 2562/0271* (2013.01); *Y02D 30/70* (2020.08); *Y10S 370/913* (2013.01)

(56) References Cited

U.S. PATENT DOCUMENTS

| | | | |
|---|---|---|---|
| 3,830,224 A | 8/1974 | Vanzetti et al. | |
| 3,845,757 A | 11/1974 | Weyer | |
| 4,121,574 A | 10/1978 | Lester | |
| 4,396,020 A | 8/1983 | Wolff et al. | |
| 4,407,295 A | 10/1983 | Steuer et al. | |
| 4,490,005 A | 12/1984 | Hovey | |
| 4,527,087 A | 7/1985 | Taya et al. | |
| 4,530,366 A | 7/1985 | Nessi et al. | |
| 4,539,996 A | 9/1985 | Engel | |
| 4,541,734 A | 9/1985 | Ishizaka | |
| 4,554,924 A | 11/1985 | Engel | |
| 4,640,289 A | 2/1987 | Craighead | |
| 4,686,998 A | 8/1987 | Robbins | |
| 4,708,146 A | 11/1987 | Lane | |
| 4,715,382 A | 12/1987 | Strand | |
| 4,765,340 A | 8/1988 | Sakai et al. | |
| 4,771,713 A | 9/1988 | Kinzenbaw | |
| 4,838,273 A | 6/1989 | Cartmell | |
| 4,846,185 A | 7/1989 | Carim | |
| 4,848,353 A | 7/1989 | Engel | |
| 4,967,765 A | 11/1990 | Turner et al. | |
| 5,012,810 A | 5/1991 | Strand et al. | |
| 5,050,612 A | 9/1991 | Matsumura | |
| 5,094,545 A | 3/1992 | Larsson et al. | |
| 5,133,356 A | 7/1992 | Bryan et al. | |
| 5,153,584 A | 10/1992 | Engira | |
| 5,215,087 A | 6/1993 | Anderson et al. | |
| 5,258,577 A | 11/1993 | Clements | |
| 5,273,036 A | 12/1993 | Kronberg et al. | |
| 5,285,577 A | 2/1994 | Carney et al. | |
| 5,344,335 A | 9/1994 | Scholz et al. | |
| 5,353,793 A | 10/1994 | Bornn | |
| 5,401,100 A | 3/1995 | Thackston et al. | |
| 5,511,553 A | 4/1996 | Segalowitz | |
| 5,544,661 A | 8/1996 | Davis et al. | |
| 5,634,468 A | 6/1997 | Platt et al. | |
| 5,803,915 A | 9/1998 | Kremenchugsky et al. | |
| 5,971,930 A | 10/1999 | Elghazzawi | |
| 5,980,467 A | 11/1999 | Henry | |
| 6,030,342 A | 2/2000 | Amano et al. | |
| 6,042,966 A | 3/2000 | Cheu | |
| 6,090,050 A | 7/2000 | Constantinides | |
| 6,222,456 B1 | 4/2001 | Tice | |
| 6,270,252 B1 | 8/2001 | Siefert | |
| 6,273,886 B1 | 8/2001 | Edwards et al. | |
| 6,287,252 B1 | 9/2001 | Lugo | |
| 6,324,426 B1 | 11/2001 | Thompson | |
| 6,355,031 B1 | 3/2002 | Edwards et al. | |
| 6,358,245 B1 | 3/2002 | Edwards et al. | |
| 6,416,471 B1* | 7/2002 | Kumar | G06F 19/323 |
| | | | 128/903 |
| 6,454,708 B1 | 9/2002 | Ferguson et al. | |
| 6,468,261 B1 | 10/2002 | Small et al. | |
| 6,472,612 B2 | 10/2002 | Fartash et al. | |
| 6,472,614 B1 | 10/2002 | Dupont et al. | |
| 6,494,829 B1 | 12/2002 | New, Jr. et al. | |
| 6,517,497 B2 | 2/2003 | Rymut et al. | |
| 6,636,754 B1 | 10/2003 | Baura et al. | |
| 6,665,802 B1* | 12/2003 | Ober | G06F 1/26 |
| | | | 713/320 |
| 6,719,701 B2 | 4/2004 | Lade | |
| 6,740,049 B2 | 5/2004 | Wallach | |
| 6,740,059 B2 | 5/2004 | Flaherty | |
| 6,950,688 B2 | 9/2005 | Axelgaard et al. | |
| 6,963,772 B2 | 11/2005 | Bloom et al. | |
| 6,980,112 B2 | 12/2005 | Nee | |
| 7,052,472 B1 | 5/2006 | Miller et al. | |
| 7,061,858 B1 | 6/2006 | Di Benedetto et al. | |
| 7,198,600 B2 | 4/2007 | Tamaki et al. | |
| 7,319,895 B2 | 1/2008 | Klefstad-Sillonville et al. | |
| 7,355,512 B1 | 4/2008 | Al-Ali | |
| RE40,470 E | 8/2008 | Fitzpatrick et al. | |
| 7,434,991 B2 | 10/2008 | Harr et al. | |
| 7,447,526 B2 | 11/2008 | Kim et al. | |
| 7,538,682 B2 | 5/2009 | Trost et al. | |
| 7,542,437 B1 | 6/2009 | Redi et al. | |
| 7,639,352 B2 | 12/2009 | Huber et al. | |
| 7,639,652 B1 | 12/2009 | Amis et al. | |
| 7,645,263 B2 | 1/2010 | Angel et al. | |
| 7,668,588 B2 | 2/2010 | Kovacs | |
| 7,924,150 B2 | 4/2011 | Baldus et al. | |
| 7,959,574 B2 | 6/2011 | Bardy | |
| 7,962,188 B2 | 6/2011 | Kiani et al. | |
| 8,007,436 B2 | 8/2011 | Katayama | |
| 8,200,320 B2 | 6/2012 | Kovacs | |
| 8,214,007 B2* | 7/2012 | Baker | A61B 5/024 |
| | | | 600/372 |
| 8,226,572 B2 | 7/2012 | Keith et al. | |
| 8,228,188 B2 | 7/2012 | Key et al. | |
| 8,231,542 B2 | 7/2012 | Keith et al. | |
| 8,496,597 B2 | 7/2013 | James et al. | |
| 8,506,480 B2 | 8/2013 | Banet et al. | |
| 8,721,562 B2 | 5/2014 | Abreu | |
| 8,909,370 B2* | 12/2014 | Stiehl | B25J 9/1671 |
| | | | 700/245 |
| 8,943,305 B2* | 1/2015 | Ho | H04L 9/0861 |
| | | | 713/151 |
| 8,968,195 B2* | 3/2015 | Tran | A61B 8/06 |
| | | | 600/300 |
| 9,055,925 B2 | 6/2015 | Paquet | |
| 9,667,065 B2* | 5/2017 | Chen | H02J 9/002 |
| 9,724,016 B1 | 8/2017 | Al-Ali | |
| 2001/0027384 A1 | 10/2001 | Schulze | |
| 2001/0047127 A1 | 11/2001 | New et al. | |
| 2002/0007676 A1 | 1/2002 | Ward et al. | |
| 2002/0013538 A1 | 1/2002 | Teller | |
| 2002/0045836 A1 | 4/2002 | Alkawwas | |
| 2002/0099277 A1 | 7/2002 | Harry et al. | |
| 2002/0107436 A1 | 8/2002 | Barton et al. | |
| 2002/0109621 A1 | 8/2002 | Khair et al. | |
| 2002/0198519 A1 | 12/2002 | Qin et al. | |
| 2003/0004403 A1 | 1/2003 | Drinan et al. | |
| 2003/0028672 A1 | 2/2003 | Goldstein | |
| 2003/0040305 A1 | 2/2003 | Ng et al. | |
| 2003/0069510 A1 | 4/2003 | Semler | |
| 2003/0191445 A1 | 10/2003 | Wallen et al. | |
| 2003/0212319 A1 | 11/2003 | Magill | |
| 2003/0212340 A1 | 11/2003 | Lussier et al. | |
| 2003/0229809 A1 | 12/2003 | Wexler et al. | |
| 2004/0015058 A1 | 1/2004 | Besson et al. | |
| 2004/0030259 A1 | 2/2004 | Dae et al. | |
| 2004/0039254 A1* | 2/2004 | Stivoric | A61B 5/0408 |
| | | | 600/300 |
| 2004/0062133 A1 | 4/2004 | Tsuji | |
| 2004/0073132 A1 | 4/2004 | Maahs et al. | |
| 2004/0116822 A1 | 6/2004 | Lindsey | |

(56) References Cited

U.S. PATENT DOCUMENTS

| | | |
|---|---|---|
| 2004/0165646 A1 | 8/2004 | Shidemantle et al. |
| 2004/0215098 A1 | 10/2004 | Barton et al. |
| 2004/0220538 A1 | 11/2004 | Panopoulos |
| 2004/0236188 A1 | 11/2004 | Hutchinson et al. |
| 2005/0085706 A1 | 4/2005 | Perrault et al. |
| 2005/0101843 A1 | 5/2005 | Quinn et al. |
| 2005/0131288 A1 | 6/2005 | Turner et al. |
| 2005/0159653 A1 | 7/2005 | Iijima et al. |
| 2005/0195079 A1 | 9/2005 | Cohen |
| 2005/0228297 A1 | 10/2005 | Banet et al. |
| 2005/0228299 A1 | 10/2005 | Banet |
| 2005/0231350 A1 | 10/2005 | Littrell et al. |
| 2005/0245831 A1 | 11/2005 | Banet |
| 2005/0245839 A1 | 11/2005 | Stivoric et al. |
| 2005/0249263 A1 | 11/2005 | Yerlikaya et al. |
| 2005/0251004 A1* | 11/2005 | Istvan ............. A61B 5/0006 600/395 |
| 2005/0251128 A1 | 11/2005 | Amoah |
| 2005/0280531 A1 | 12/2005 | Fadem et al. |
| 2006/0009697 A1 | 1/2006 | Banet et al. |
| 2006/0031102 A1 | 2/2006 | Teller |
| 2006/0045165 A1 | 3/2006 | Chan et al. |
| 2006/0047987 A1 | 3/2006 | Prabhakaran et al. |
| 2006/0094971 A1 | 5/2006 | Drew |
| 2006/0098576 A1 | 5/2006 | Brownrigg et al. |
| 2006/0155183 A1 | 7/2006 | Kroecker et al. |
| 2006/0202816 A1 | 9/2006 | Crump et al. |
| 2006/0224349 A1 | 10/2006 | Butterfield |
| 2006/0276714 A1 | 12/2006 | Holt et al. |
| 2007/0032706 A1 | 2/2007 | Kamath et al. |
| 2007/0041424 A1 | 2/2007 | Lev et al. |
| 2007/0099678 A1 | 5/2007 | Kim et al. |
| 2007/0116089 A1 | 5/2007 | Bisch et al. |
| 2007/0123756 A1 | 5/2007 | Kitajima et al. |
| 2007/0129622 A1 | 6/2007 | Bourget et al. |
| 2007/0135866 A1* | 6/2007 | Baker ............... A61B 5/0002 607/60 |
| 2007/0142715 A1 | 6/2007 | Banet et al. |
| 2007/0185660 A1 | 8/2007 | Anderson |
| 2007/0191728 A1 | 8/2007 | Shennib |
| 2007/0208233 A1 | 9/2007 | Kovacs |
| 2007/0219434 A1 | 9/2007 | Abreu |
| 2007/0225614 A1 | 9/2007 | Naghavi et al. |
| 2007/0293781 A1 | 12/2007 | Sims et al. |
| 2008/0042866 A1 | 2/2008 | Morse et al. |
| 2008/0091090 A1 | 4/2008 | Guillory et al. |
| 2008/0097178 A1 | 4/2008 | Banet et al. |
| 2008/0097422 A1 | 4/2008 | Edwards et al. |
| 2008/0114220 A1 | 5/2008 | Banet et al. |
| 2008/0119707 A1 | 5/2008 | Stafford |
| 2008/0143512 A1 | 6/2008 | Wakisaka et al. |
| 2008/0183054 A1 | 7/2008 | Kroeger et al. |
| 2008/0200770 A1 | 8/2008 | Hubinette |
| 2008/0200774 A1 | 8/2008 | Luo |
| 2008/0208026 A1 | 8/2008 | Noujaim et al. |
| 2008/0214949 A1 | 9/2008 | Stivoric et al. |
| 2008/0221399 A1 | 9/2008 | Zhou et al. |
| 2008/0234600 A1 | 9/2008 | Marsh |
| 2008/0275327 A1 | 11/2008 | Faarbaek et al. |
| 2008/0294058 A1 | 11/2008 | Shklarski |
| 2008/0294065 A1 | 11/2008 | Waldhoff et al. |
| 2008/0305154 A1 | 12/2008 | Yanaki |
| 2009/0018409 A1 | 1/2009 | Banet et al. |
| 2009/0024345 A1* | 1/2009 | Prautzsch ............. H05K 1/0207 702/99 |
| 2009/0054737 A1 | 2/2009 | Magar et al. |
| 2009/0059827 A1* | 3/2009 | Liu ..................... H04W 76/28 370/311 |
| 2009/0062670 A1 | 3/2009 | Sterling et al. |
| 2009/0069642 A1 | 3/2009 | Gao et al. |
| 2009/0073991 A1 | 3/2009 | Landrum |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076350 A1* | 3/2009 | Bly ..................... A61B 5/04085 600/301 |
| 2009/0076363 A1 | 3/2009 | Bly et al. |
| 2009/0076364 A1 | 3/2009 | Libbus et al. |
| 2009/0076405 A1 | 3/2009 | Amurthur et al. |
| 2009/0076559 A1 | 3/2009 | Libbus et al. |
| 2009/0105549 A1 | 4/2009 | Smith et al. |
| 2009/0105605 A1 | 4/2009 | Abreu |
| 2009/0131759 A1 | 5/2009 | Sims et al. |
| 2009/0131774 A1 | 5/2009 | Sweitzer et al. |
| 2009/0182204 A1 | 7/2009 | Semler et al. |
| 2009/0203974 A1 | 8/2009 | Hickle |
| 2009/0209896 A1 | 8/2009 | Selevan |
| 2009/0227877 A1 | 9/2009 | Tran |
| 2009/0259139 A1 | 10/2009 | Stepien et al. |
| 2009/0270744 A1 | 10/2009 | Prstojevich et al. |
| 2009/0271681 A1 | 10/2009 | Piret et al. |
| 2009/0306536 A1 | 12/2009 | Ranganathan et al. |
| 2010/0010319 A1 | 1/2010 | Tivig et al. |
| 2010/0036212 A1 | 2/2010 | Rieth |
| 2010/0052615 A1* | 3/2010 | Loncarevic .......... H02J 7/0016 320/118 |
| 2010/0056886 A1 | 3/2010 | Hurtubise et al. |
| 2010/0056945 A1 | 3/2010 | Holmes |
| 2010/0056946 A1 | 3/2010 | Holmes |
| 2010/0056947 A1 | 3/2010 | Holmes |
| 2010/0081949 A1 | 4/2010 | Derby, Jr. |
| 2010/0100004 A1 | 4/2010 | van Someren |
| 2010/0113894 A1 | 5/2010 | Padiy |
| 2010/0121217 A1 | 5/2010 | Padiy et al. |
| 2010/0160745 A1 | 6/2010 | Hills et al. |
| 2010/0222688 A1 | 9/2010 | Fischell et al. |
| 2010/0234716 A1 | 9/2010 | Engel |
| 2010/0249541 A1 | 9/2010 | Geva et al. |
| 2010/0249625 A1 | 9/2010 | Lin |
| 2010/0286607 A1 | 11/2010 | Saltzstein |
| 2010/0292605 A1 | 11/2010 | Grassl et al. |
| 2010/0298656 A1 | 11/2010 | McCombie et al. |
| 2010/0298895 A1 | 11/2010 | Ghaffari et al. |
| 2010/0323634 A1 | 12/2010 | Kimura |
| 2010/0324548 A1 | 12/2010 | Godara et al. |
| 2011/0004076 A1 | 1/2011 | Janna et al. |
| 2011/0060252 A1 | 3/2011 | Simonsen et al. |
| 2011/0066062 A1 | 3/2011 | Banet et al. |
| 2011/0077497 A1 | 3/2011 | Oster et al. |
| 2011/0144470 A1 | 6/2011 | Mazar et al. |
| 2011/0160601 A1 | 6/2011 | Wang et al. |
| 2011/0176465 A1 | 7/2011 | Panta et al. |
| 2011/0182213 A1 | 7/2011 | Forssell et al. |
| 2011/0224557 A1 | 9/2011 | Banet et al. |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029308 A1 | 2/2012 | Paquet |
| 2012/0029309 A1 | 2/2012 | Paquet |
| 2012/0029310 A1 | 2/2012 | Paquet et al. |
| 2012/0029311 A1 | 2/2012 | Raptis et al. |
| 2012/0029312 A1 | 2/2012 | Beaudry et al. |
| 2012/0029313 A1 | 2/2012 | Burdett et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0030547 A1 | 2/2012 | Raptis et al. |
| 2012/0108920 A1 | 5/2012 | Bly et al. |
| 2012/0165621 A1 | 6/2012 | Grayzel et al. |
| 2012/0238901 A1 | 9/2012 | Augustine |
| 2012/0310070 A1 | 12/2012 | Kumar et al. |
| 2014/0350362 A1 | 11/2014 | Raptis et al. |
| 2015/0272515 A1 | 10/2015 | Paquet et al. |

FOREIGN PATENT DOCUMENTS

| | | |
|---|---|---|
| JP | 2002507131 A | 3/2002 |
| JP | 2004503266 A | 2/2004 |
| JP | 2005521453 A | 7/2005 |
| JP | 2009544065 A | 12/2009 |

(56) References Cited

FOREIGN PATENT DOCUMENTS

| KR | 20070097725 A | 10/2007 |
|---|---|---|
| KR | 100949150 B1 | 3/2010 |
| WO | WO-1990012606 A2 | 11/1990 |

OTHER PUBLICATIONS

Arisha, K. et al. in "System-Level Power Optimization for wireless Multimedia Communicatioin". Editors: Ramesh, K and Goodman, D.; Springer US; 2002, p. 21-40.
Brown, B.H. et al., "Bipolar and Tetrapolar transfer impedence measurements from volume conductor," Electronics Letters, Wol. 35, No. 25, 2000, pp. 2060-2062.
Cardei, M. et al; "Improving Wireless Sensor Network Lifteim through Power Aware Ogranization"; Wireless Networks 11, 333-340, 2005.
Cooley, W.L. et al. "A new design for an impedence pneumograph," Journal of Applied Physiology, vol. 25, No. 4, 1968, pp. 429-432.
Davidson, K.G. et al., "Measurement of tidal volume by using transthoracic impedance variations in rats," J. Appl. Physiol. 86: 759-766, 1999.
Ernst, J.M. et al, "Impedance Penumography; noise as signal in impednace cardiography," Psychophysiology, 36 (1999) 333-338.
Freundlich J.J. et al., Electrical Impedance Pneumography for Simple Nonrestritive Continuous Monitoring of Respiratory Rate, Rhythm and Tidal Volume for Surgical Patients, Chest, 65, p. 181-184, 1974.
Grenvik, A. et al., "Impedence Pneumography," Chest , vol. 62, No. 4, Oct. 1972, pp. 439-443.
Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.
Hohlt, B. et al. "Flexible Power Scheduling for Sensor Networks", IPSN'04, Apr. 26-27, 2004, Berkeley, California, USA. p. 1-10.
Holt, T. et al., "Monitoring and recording of physiological data of the manned space flight program," Supplement to IEEE Transactions on Aerospace, Jun. 1965, p. 341-344.
International Preliminary Report on Patentability in International Application No. PCT/US2011/030088, dated Oct. 27, 2012, 13 pages.
International Preliminary Report on Patentability in International Application No. PCT/US2011/045240, dated Jan. 29, 2013, 6 pages.
International Preliminary Report on Patentability in International Application No. PCT/US2011/045245, dated Jan. 29, 2013, 5 pages.
International Preliminary Report on Patentability in International Application No. PCT/US2011/045249, dated Jan. 29, 2013, 4 pages.
International Preliminary Report on Patentability in International Application No. PCT/US2011/045256, dated Jan. 29, 2013, 4 pages.
International Preliminary Report on Patentability in International Application No. PCT/US2011/045258, dated Jan. 29, 2013, 5 pages.
International Preliminary Report on Patentability in International Application No. PCT/US2011/045337, dated Jan. 9, 2013, 4 pages.
International Preliminary Report on Patentability in International Application No. PCT/US2011/045361, dated Jan. 29, 2013, 6 pages.
International Preliminary Report on Patentability in International Application No. PCT/US2011/045408, dated Jan. 29, 2013, 4 pages.
International Preliminary Report on Patentability in International Application No. PCT/US2011/045414, dated Jan. 29, 2013, 6 pages.
International Preliminary Report on Patentability in International Application No. PCT/US2011/045415, dated Jan. 29, 2013, 4 pages.
International Preliminary Report on Patentability in International Application No. PCT/US2011/045419, dated Jan. 29, 2013, 5 pages.
International Preliminary Report on Patentability in International Application No. PCT/US2011/045425, dated Jan. 29, 2013, 5 pages.
International Search Report and Written Opinion for International Application No. PCT/US2011/045408, dated Feb. 24, 2012, 6 pages.
International Search Report and Written Opinion in International Application No. PCT/US2011/045361, dated Apr. 6, 2012, 8 pages.
International Search Report and Written Opinion in International Application No. PCT/US2011/030088, dated Oct. 31, 2011, 7 pages.
International Search Report and Written Opinion in International Application No. PCT/US2011/045240, dated Mar. 15, 2012, 8 pages.
International Search Report and Written Opinion in International Application No. PCT/US2011/045245, dated Mar. 28, 2012, 7 pages.
International Search Report and Written Opinion in International Application No. PCT/US2011/045249, dated Mar. 12, 2012, 6 pages.
International Search Report and Written Opinion in International Application No. PCT/US2011/045256, dated Feb. 9, 2012, 12 pages.
International Search Report and Written Opinion in International Application No. PCT/US2011/045258, dated Apr. 6, 2012, 12 pages.
International Search Report and Written Opinion in International Application No. PCT/US2011/045337, dated Feb. 9, 2012, 7 pages.
International Search Report and Written Opinion in International Application No. PCT/US2011/045414, dated Feb. 24, 2012, 9 pages.
International Search Report and Written Opinion in International Application No. PCT/US2011/045415, dated Feb. 24, 2012, 7 pages.
International Search Report and Written Opinion in International Application No. PCT/US2011/045419, dated Apr. 6, 2012, 7 pages.
International Search Report and Written Opinion in International Application No. PCT/US2011/045425, dated Apr. 6, 2012, 7 pages.
Kelkar, S.P. et al., "Development of Movement artifact free breathing monitor," J. Instrum. Soc. India 38(1) 34-43, 2008.
Kessler, "TCP/IP and tcpdump Pocket reference Guide", Champlain College, 2006.
Lee, W. L. et al; "FlexiTP: A Flexible-Schedule-Based TDMA Protocol for Fault-Tolerant and energy-Efficient Wireless Sensor Networks", IEEE transactions on Parallel and Distributed Systems, vol. 19, No. 6, Jun. 2008; p. 851-864.
Lee, W.L.; "Flexible-Schedule-Based TDMA Protocols for Supporting Fault-Tolerance, On-Demand TDMA Slot Transfer, and Peer-to-Peer Communication in Wireless Sensor Networks"; Thesis for the degree of Doctor in Philosophy, University of Western Australia, 2007, p. 1-213.
Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, p. 7349-7352.
Luo, S. et al "The electrode system in Impedance-Based Ventilation Measurement", IEEE Transactions of Biomedical Engineering, vol. 39, No. 11, Nov. 1992, p. 1130-1140.
Matthews, R., et al., "A Wearable Physiological Sensor Suite for Unobstrusive Monitoring of Physiological and Cognitive State," Proceedings of the 29th annual International Conference of the IEEE EMBS Cite Internationale, Lyon, France, Aug. 23-26, 2007.
Miller, Matthew J., et al., "On-Demand TDMA Scheduling for energy Conservation in Sensor Networks," Technical Report, Jun. 2004.
Murat, B., "Electrical Impedance Plethysmography," Wiley Encyclopedia of Biomedical Engineering , 2006, p. 1-10.
NPL_VitalSense_2006, p. 1-2.
Pacela, A. "Impedance Pneumogrpahy—a survey of Instrumentation Techniques" Med. & Biol. Engng. vol. 4, pp. 1-15, 1996.
Pantazis, N. A. et al; "Energy efficiency in wireless sensor networks using sleep mode TDMA scheduling", Ad Hoc Networks 7 (2009) 322-343.
Paradiso, R. et al. "A wearalbe health care system based on knitted integrated sensors", IEEE transactions on Information Technology in Biomedicine, vol. 9, No. 3, Sep. 2005, p. 337-344.
Park, et al., "Development of Flexible Self Adhesive Patch for Professional Heat Stress Monitoring Service," Proceedings of the

(56) References Cited

OTHER PUBLICATIONS

2005 IEEE Engineering in Medicine and Biology 27th Annual Conference Shanghai, China, Sep. 1-4, 2005, pp. 3789-3792.
Poon, C.S. et al., "Evaluation of two noninvasive techniques for exercise ventilatory measurements," IEEE Engineering in Medicine and Biology Conference, 1988, pp. 0823-0824.
Rashid, R. A. et al; "Development of Energy Aware TDMA-Based MAC Protocol for Wireless Sensor Network System", European Journal of Scientific Research, vol. 30 No. 4 (2009), pp. 571-578.
Shakian, A.V. et al., "electrode Motion Artifacts in electrical Impedence Pneumography," IEEE Transactions in Biomedical Engineering, vol. BME-32, No. 6, Jun. 1985, pp. 448-451.
Shaw, G.A. et al., "Warfighter Physiological and Environmental Monitoring: A Study for the U.S. Army Research Institute in Environmental Medicine and the Soldier Systems Center," 2004, Lincoln Laboratory, MIT, pp. 1-141.
Zheng, W.W. et al; "Adaptive-frame based Dynamic Slot Assignment Protocol for Tactical Data Link Systems", 2009 International Conference on Networks Security, Wireless Communications and Trusted Computing, IEEE, p. 709-714.
Zhihui Chen; Kohkhar, A. "Self organization and energy efficient TDMA MAC protocol by wake up for wireless sensor networks," Sensor and Ad Hoc Communications and Networks, 2004. IEEE Secon 2004. 2004 First Annual IEEE Communications Society Conference on, pp. 335-341, Oct. 2004.
W. J. Tompkins, Biomedical Digital Signal Processing. Prentice Hall, New Jersey, 1993; p. 1-378 (Year: 1993).

\* cited by examiner

SYSTEM AND METHOD FOR SAVING BATTERY POWER IN A PATIENT MONITORING SYSTEM

CROSS-REFERENCES TO RELATED APPLICATIONS

This application is a divisional of U.S. patent application Ser. No. 12/844,801 filed Jul. 27, 2010, which issued as U.S. Pat. No. 9,017,255 on Apr. 28, 2015, which is herein incorporated by reference in its entirety for all purposes.

BACKGROUND

Field

The present disclosure generally relates to systems and methods of physiological monitoring, and, in particular, relates to monitoring of vital signs of patients in hospitals.

Description of the Related Art

Some of the most basic indicators of a person's health are those physiological measurements that reflect basic body functions and are commonly referred to as a person's "vital signs." The four measurements commonly considered to be vital signs are body temperature, pulse rate, blood pressure, and respiratory rate. Some clinicians consider oxygen saturation ($S_{O2}$) to be a "fifth vital sign" particularly for pediatric or geriatric cases. Some or all of these measurements may be performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time which is then converted to a "per minute" rate. If a patient's pulse is weak, it may not be possible to detect a pulse by hand and the nurse may use a stethoscope to amplify the sound of the patient's heart beat so that she can count the beats. Oxygen saturation of the blood is most easily measured with a pulse oximeter.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more-serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Another method of taking a body temperature is by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use 12 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wristwatch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need for a hospital to be able to continuously monitor its patients in different settings within the hospital. In addition, it is desirable for this monitoring to be done with limited interference with a patient's mobility or interfering with their other activities.

Continuous monitoring implies that the sensors that measure the physiological characteristic of interest remain continuously in place on the patient. Periodic removal of a sensor, for such things as using the bathroom or showering, usually requires a nurse or other caregiver to reattach the sensor to ensure that the sensor is properly attached and may require replacement of the sensor each time the sensor is removed. The presence of wires between the sensors and the monitoring equipment makes it difficult for a patient to perform their normal activities and move around the hospital. An analogous situation exists in use of an intravenous (IV) system to continuously administer medication, where the patient is connected to an IV bag via a tube which remains continuously attached to the patient. Even when the IV bag is mounted on a mobile stand without connection to a fixed piece of equipment, this attached tube poses a significant impediment to a patient in moving around the hospital, changing clothes, and taking a shower.

One solution to the problem of providing continuous monitoring without having wires connecting the patient to separate device is to use a battery-powered wireless device to measure the physiological characteristics of interest. The useful life of battery-powered devices is limited, however, by the capacity of the battery compared to the power consumption of the device. Providing a battery-powered device that can monitor the vital signs of a patient for a period of several days may require a battery so large that it is impractical for the patient to continuously wear the device. It is highly desirable to provide a vital-signs monitoring device that has a very low level of power consumption such that a very small battery, such as the "coin" batteries commonly used in watches, has enough power to continuously operate the device for several days.

Embodiments of the patient monitoring system disclosed herein measure certain vital signs of a patient, which include respiratory rate, pulse rate, and body temperature, on a regular basis and compare these measurements to preset limits.

In certain embodiments of the disclosure, a vital-signs patch for a patient monitoring system is disclosed. The patch consists of a housing that is configured to be worn on the skin of a patient. The housing contains a radio, one or more sensor interfaces, a processor, and a battery. The processor can selectably turn portions of the processor off and on and selectably turn power off and on to at least a portion of the sensor interfaces and radio. The processor includes a timer that, each time the timer times out, will turn all the parts of the processor on and start a new timing period. When the processor receives a signal, the processor will turn off power to at least a portion of the processor and at least a portion of the sensor interfaces.

In certain embodiments of the disclosure, a patient monitoring system is disclosed. The system includes a patch configured to turn off a portion of its circuitry for a period of time upon receipt of a sleep signal and then to turn on that portion of its circuitry after a period of time has elapsed, and a bridge configured to send the sleep signal to the patch. The bridge tracks when the period of time elapses and sends the sleep signal to the patch after the period of time elapses.

In certain embodiments of the disclosure, a method of conserving battery power in a patch in a patient monitoring system is disclosed. The method includes the steps of the patch receiving a sleep signal, turning off a portion of the circuitry of the patch and starting a timer, turning on the portion of the circuitry that was turned off upon the timer timing out, and resumption of monitoring for sleep signals.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
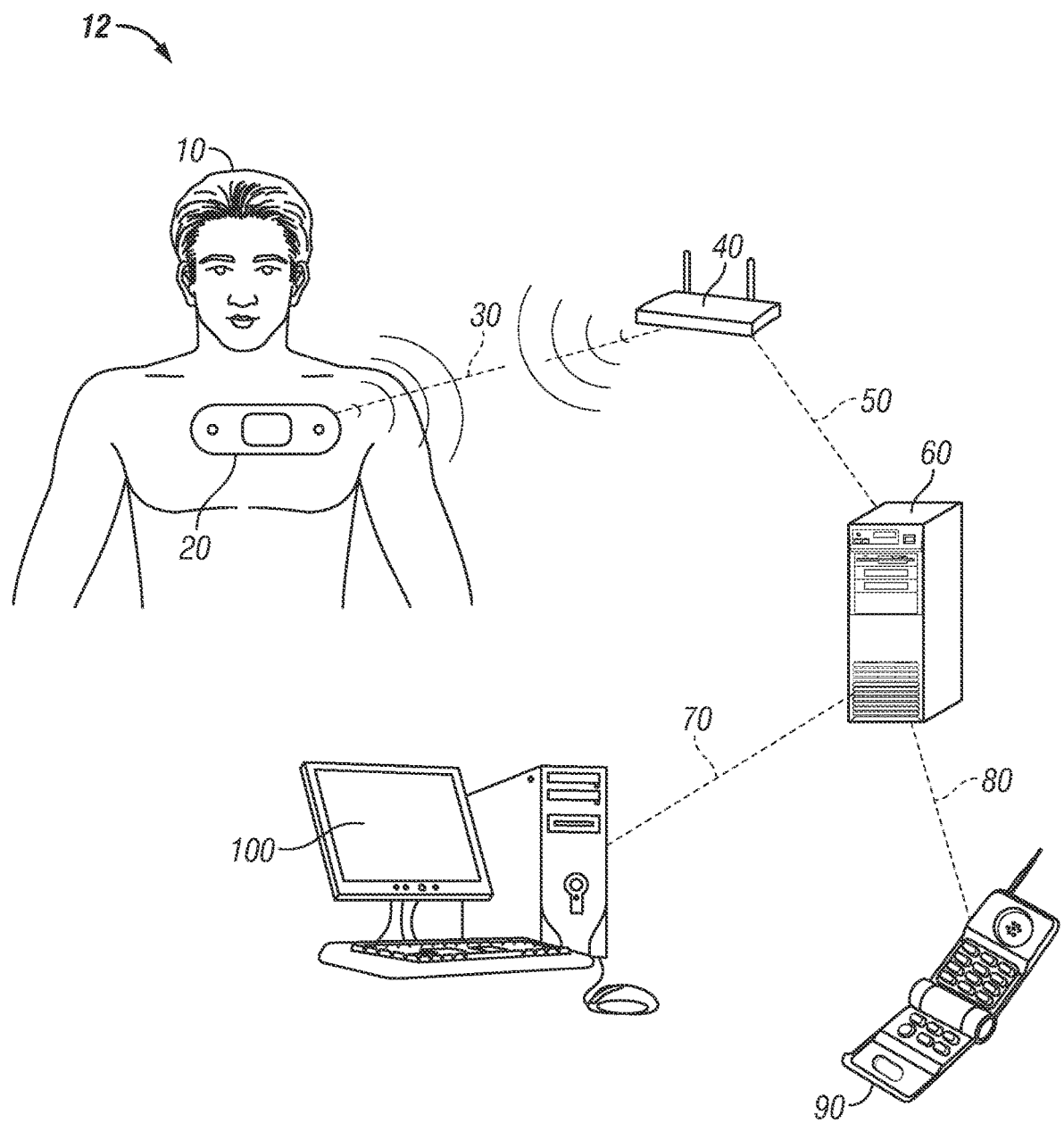
FIG. 1 is a diagram illustrating an exemplary embodiment of a patient monitoring system according to certain aspects of the present disclosure.

Periodic monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 12 electrodes placed at various points on the body to detect various signals associated with the cardiac function. Another common piece of equipment is termed a "heart rate monitor." Widely sold for use in exercise and physical training, heart rate monitors may comprise a torso band in which are embedded two electrodes held against the skin and a small electronics package. Such heart rate monitors can communicate wirelessly to other equipment such as a small device that is worn like a wristwatch and that can transfer data wirelessly to a personal computer (PC).

Monitoring of patients that is referred to as "continuous" is frequently periodic, in that measurements are taken at intervals. In many cases, the process to make a single measurement takes a certain amount of time, such that even back-to-back measurements produce values at an interval equal to the time that it takes to make the measurement. For the purpose of vital sign measurement, a sequence of repeated measurements can be considered to be "continuous" when the vital sign is not likely to change an amount that is of clinical significance within the interval between measurements. For example, a measurement of blood pressure every 10 minutes may be considered "continuous" if it is considered unlikely that a patient's blood pressure can change by a clinically significant amount within 10 minutes. The interval appropriate for measurements to be considered continuous may depend on a variety of factors including the type of injury or treatment and the patient's medical history. Compared to intervals of 4-8 hours for manual vital sign measurement in a hospital, measurement intervals of 30 minutes to several hours may still be considered "continuous."

Certain exemplary embodiments of the present disclosure include a system that comprises a vital-signs monitor patch that is attached to the patient, and a bridge that communicates with monitor patches and links them to a central server that processes the data, where the server can send data and alarms to a hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital signs such as cardiac pulse rate and respiration rate. Monitor patch 20 also may include other sensors such as an accelerometer, temperature sensor, or oxygen saturation sensor to measure other characteristics associated with the patient. These other sensors may be internal to the monitor patch 20 or external sensors that are operably connected to the monitor patch 20 via a cable or wireless connection. Monitor patch 20 also includes a wireless transmitter that can both transmit and receive signals. This transmitter is preferably a short-range, low-power radio frequency (RF) device operating in one of the unlicensed radio bands. One band in the United States (US) is, for example, centered at 915 MHz and designated for industrial, scientific and medical (ISM) purposes. An example of an equivalent band in the European Union (EU) is centered at 868 MHz. Other frequencies of operation may be possible dependent upon the International Telecommunication Union (ITU), local regulations and interference from other wireless devices.

Surveillance server 60 may be a standard computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 10 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hard-wired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), laptops, or smart phones, over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
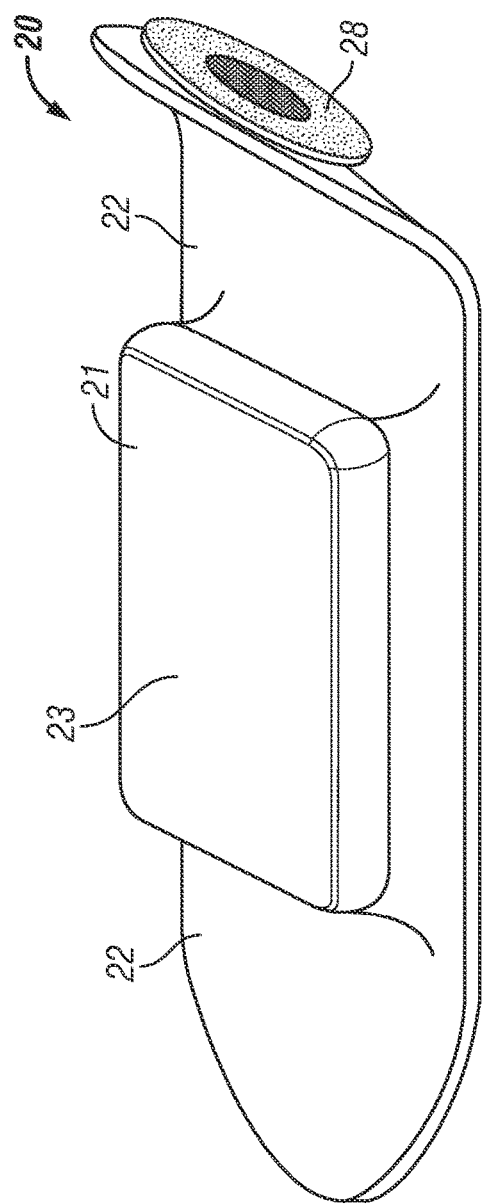
FIG. 2A is a perspective view of the vital-signs monitor patch of FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 2B) having electronic components and battery mounted to a rigid printed circuit board (PCB). The side segments 22 are flexible and include a flexible conductive circuit (26, FIG. 2B) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
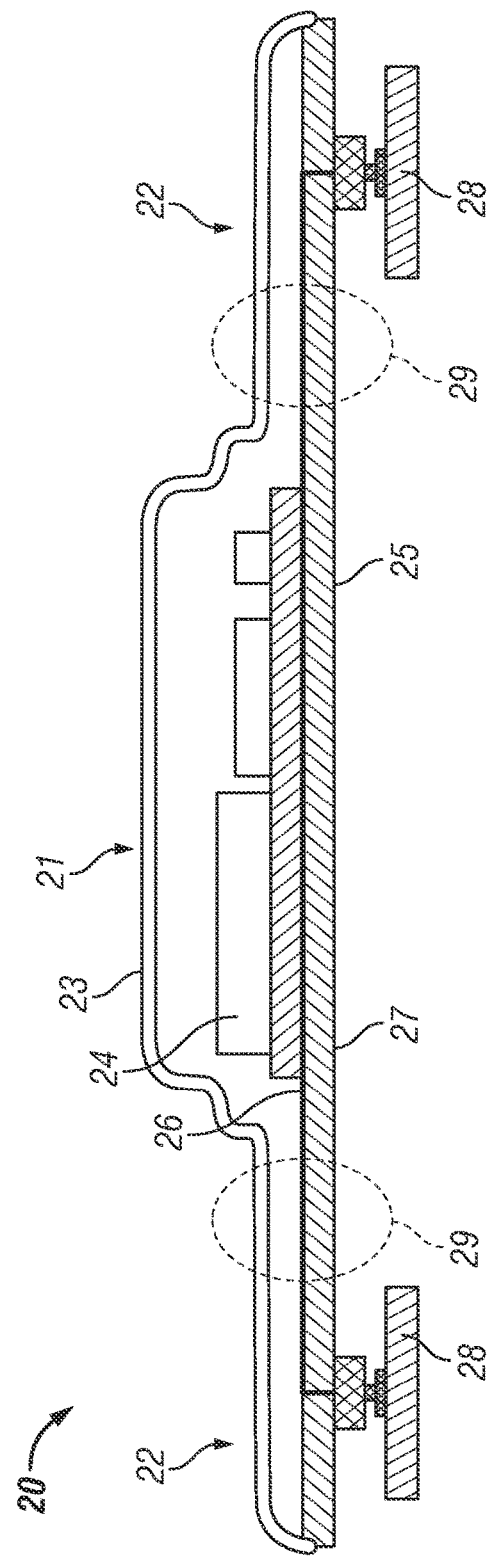
FIG. 2B is a cross-section of the vital-signs monitor patch of FIG. 1 according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
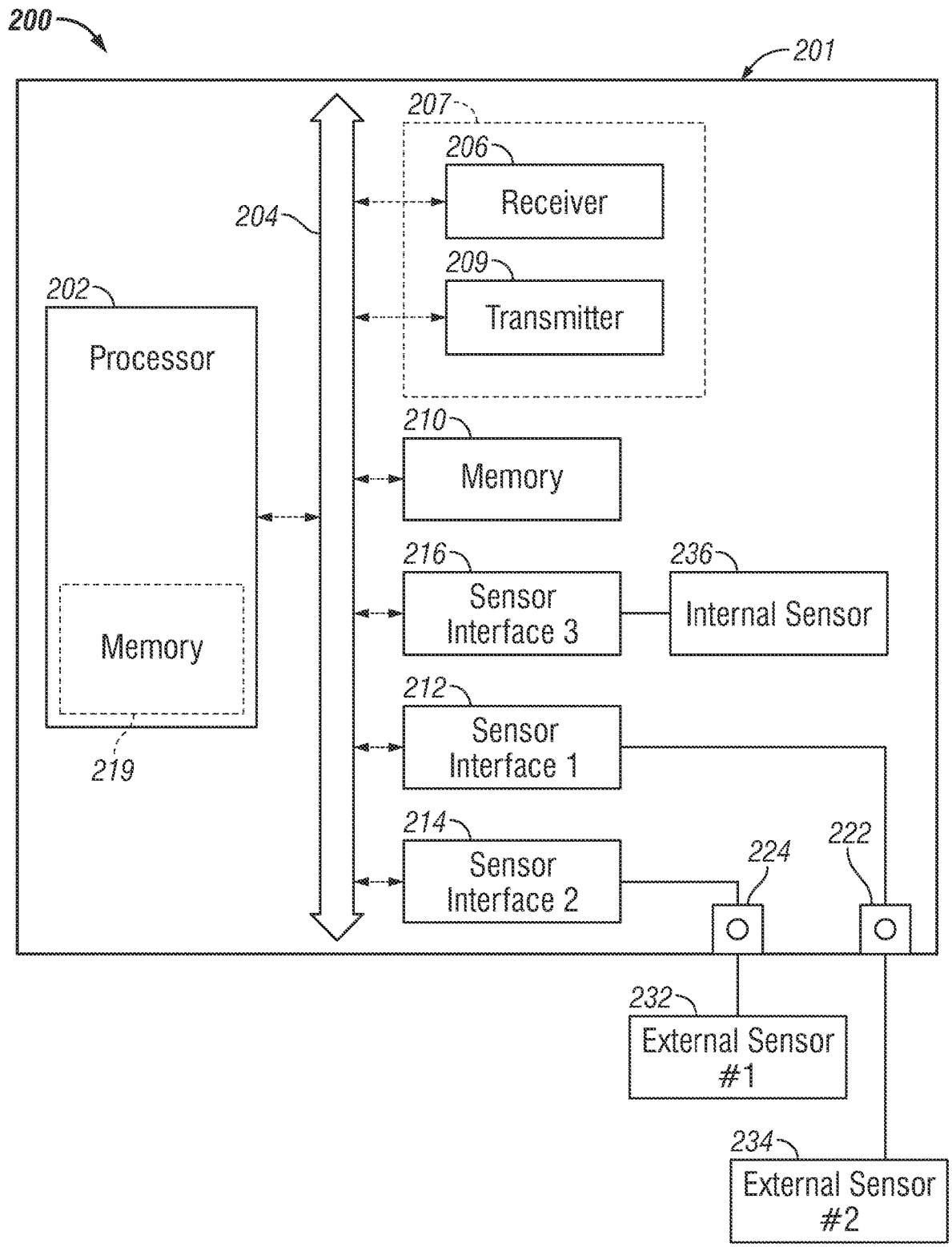
FIG. 2C is a functional block diagram illustrating exemplary electronic and sensor components of the vital-signs monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of a RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202. In other embodiments, the radio may comprise a direct sequence radio, a software-defined radio, or an impulse spread spectrum radio.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion or position with respect to gravity.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor or resistive thermal device (RTD)) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure, pulse rate, or oxygen saturation.

Figure 3A:
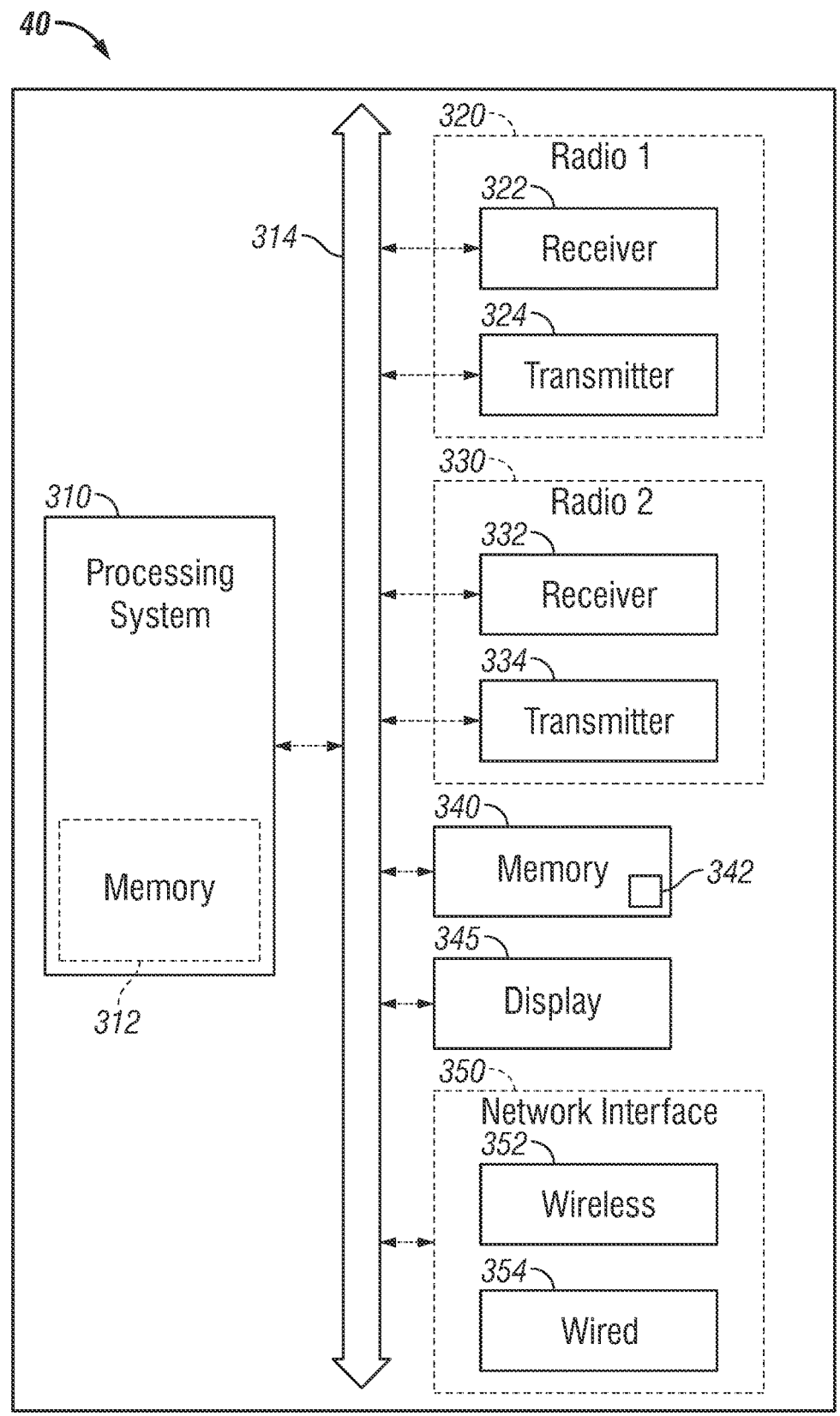
FIG. 3A is a functional schematic diagram of the bridge according to certain aspects of the subject disclosure.

FIG. 3A is a functional block diagram illustrating exemplary electronic components of bridge 40 of FIG. 1 according to certain aspects of the subject disclosure. Bridge 40 includes a processor 310, radio 320 having a receiver 322 and a transmitter 324, radio 330 having a receiver 332 and a transmitter 334, memory 340, display 345, and network interface 350 having a wireless interface 352 and a wired interface 354. In some embodiments, some or all of the aforementioned components of module 300 may be integrated into single devices or mounted on PCBs.

Processor 310 is configured to send data to and receive data from receiver 322 and transmitter 324 of radio 320, receiver 332 and transmitter 334 of radio 330 and wireless interface 352 and wired interface 354 of network interface 350 via bus 314. In certain embodiments, transmitters 324 and 334 may include a radio frequency signal generator (oscillator), a modulator, and a transmitting antenna, and the receivers 322 and 332 may include a demodulator and antenna which may or may not be the same as the transmitting antenna of the radio. In some embodiments, transmitters 324 and 334 may include a digital-to-analog converter configured to convert data received from processor 310 and to generate a base signal, while receivers 322 and 332 may include analog-to-digital converters configured to convert a demodulated base signal and sent a digitized data stream to processor 310.

Processor 310 may include a general-purpose processor or a specific-purpose processor for executing instructions and may further include a memory 312, such as a volatile or non-volatile memory, for storing data and/or instructions for software programs. The instructions, which may be stored in memories 312 or 340, may be executed by the processor 310 to control and manage the transceivers 320, 330, and 350 as well as provide other communication and processing functions.

Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 312 internal to processor 310 or in memory 340 external to processor 310 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 312 or 340 can also store a list or a database of established communication links and their corresponding characteristics (e.g., signal levels) between the bridge 40 and its related monitor patches 20. In the illustrated example of FIG. 3A, the memory 340 external to the processor 310 includes such a database 342; alternatively, the memory 312 internal to the processor 310 may include such a database.

Figure 3B:
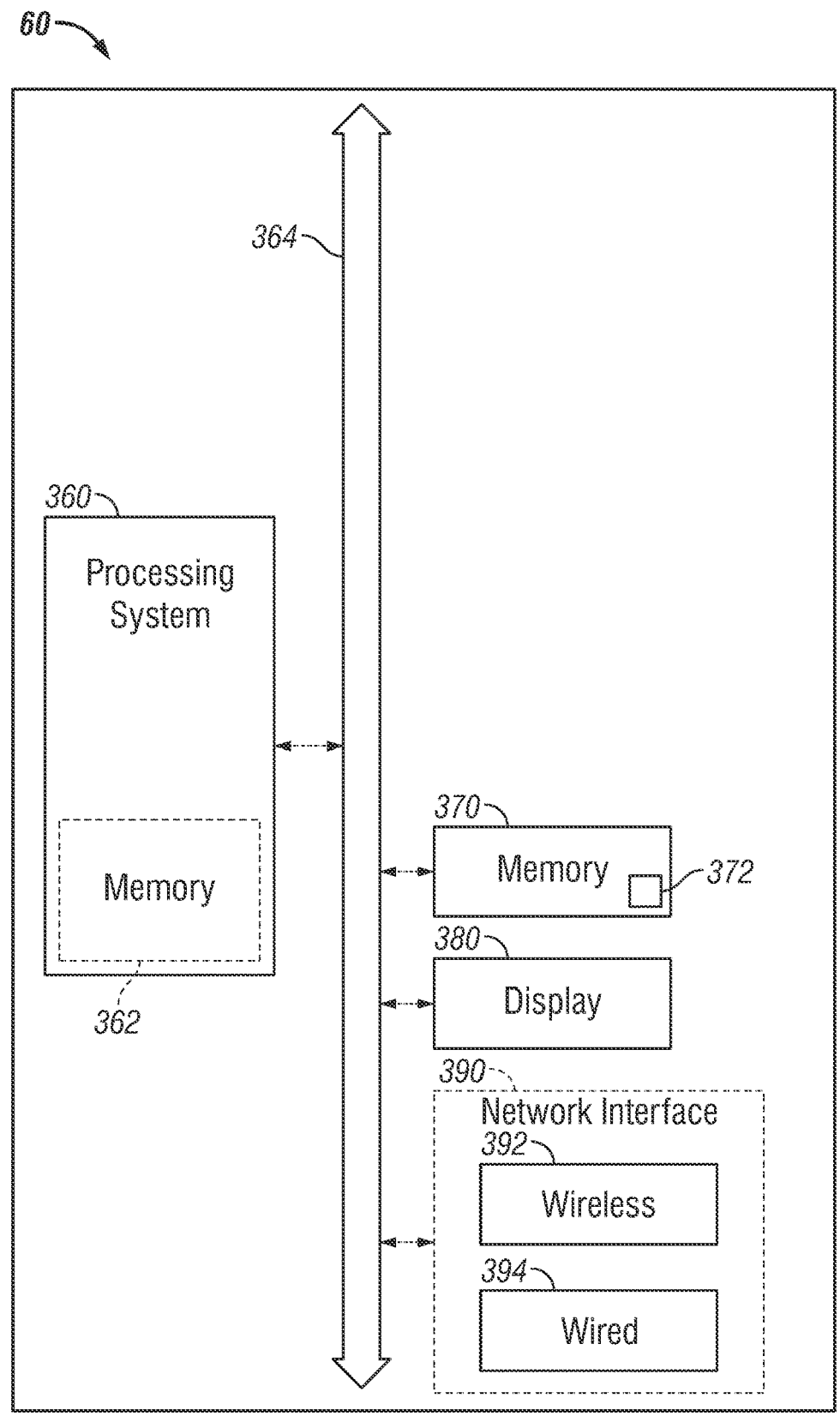
FIG. 3B is a functional schematic diagram of an embodiment of the surveillance server according to certain aspects of the present disclosure.

FIG. 3B is a functional block diagram illustrating exemplary electronic components of server 60 of FIG. 1 according to one aspect of the subject disclosure. Server 60 includes a processor 360, memory 370, display 380, and network interface 390 having a wireless interface 392 and a wired interface 394. Processor 360 may include a general-purpose processor or a specific-purpose processor for executing instructions and may further include a memory 362, such as a volatile or non-volatile memory, for storing data and/or instructions for software programs. The instructions, which may be stored in memories 362 or 370, may be executed by the processor 360 to control and manage the wireless and wired network interfaces 392, 394 as well as provide other communication and processing functions.

Processor 360 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 362 internal to processor 360 or in memory 370 external to processor 360 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 362 or 370 can also store a database of communication links and their corresponding characteristics (e.g., signal levels) between monitor patches 20 and bridges 40. In the illustrated example of FIG. 3B, the memory 370 external to the processor 360 includes such a database 372; alternatively, the memory 362 internal to the processor 360 may include such a database.

Figure 4:
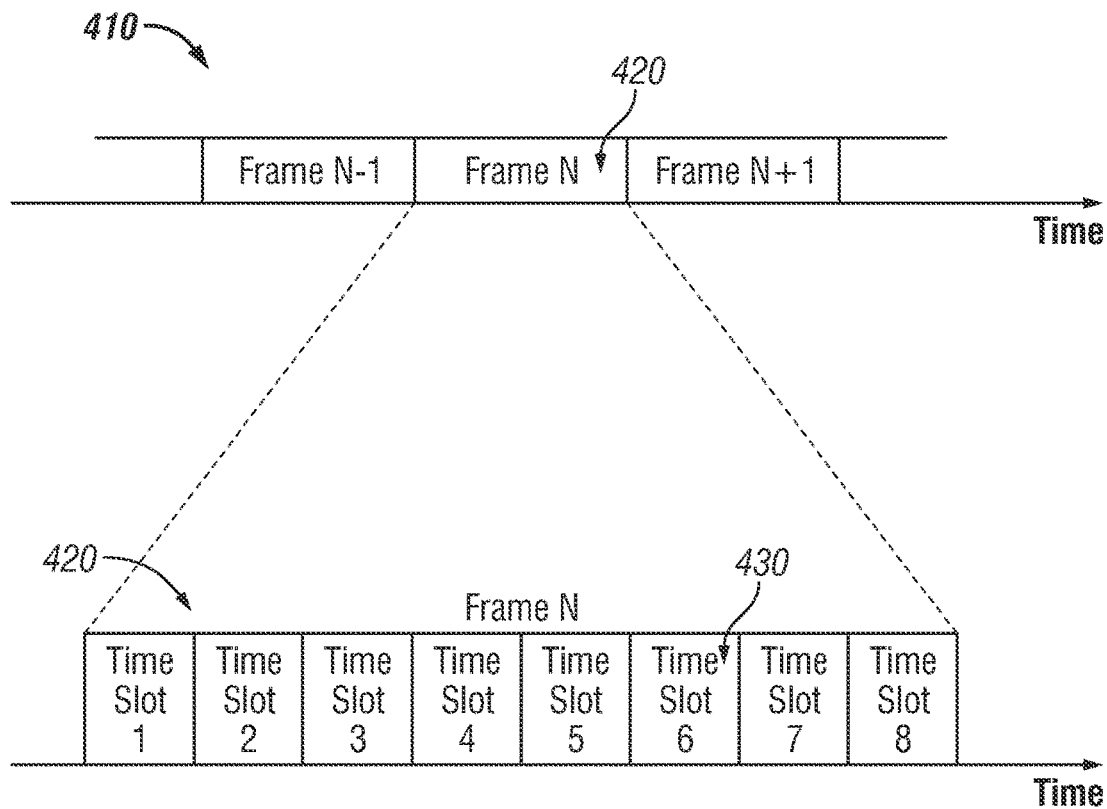
FIG. 4 discloses an example of the communication protocol between the vital-signs patch and bridge according to certain aspects of the present disclosure.

FIG. 4 discloses certain aspects of the communication protocol between patch 20 and bridge 40. Bridge 40 may be configured to communicate with multiple patches 20. Bridge 40 will define a length of time during which it will allocate time to communicate with each patch 20. This defined period of time 420 is termed a 'frame' and FIG. 4 illustrates how a data stream 410 is segmented into frames 420 that are sequentially arranged and numbered. Frame N is preceded by frame N−1 and followed by frame N+1. Each frame 420 has an identical internal structure which, in this example, has been configured to enable bridge 40 to communicate with up to eight patches. Frame 420 has been segmented into eight time slots 430, numbered 1-8 in this example, as shown in the expanded view of frame 420. Each patch 20 which is in communication with bridge 40 is assigned to a time slot 430 by bridge 40.

Figure 5:
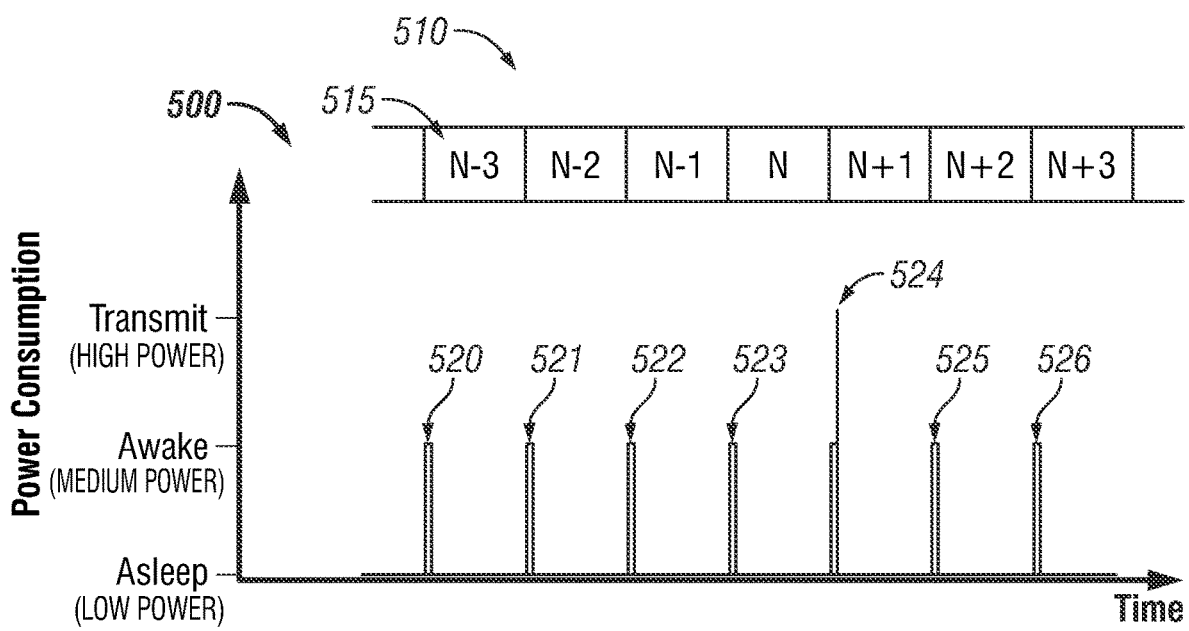
FIG. 5 is a plot of power consumption vs. time illustrating that battery power in the vital-signs patch is conserved according to certain aspects of this disclosure.

FIG. 5 discloses how battery power is conserved according to certain aspects of this disclosure. Plot 500 illustrates the instantaneous power consumption of a patch 20, with time plotted on the horizontal axis and power plotted on the vertical axis. The frame sequence 410 from FIG. 4 is repeated as timeline 510 as a reference. In timeline 510, the patch 20 whose power is plotted in plot 500 has been assigned to time slot 515 which is the first time slot in each frame and is darkened in each frame of timeline 510.

At the beginning of each time slot 430, the entire electronics of patch 20 are turned on. Patch 20 sends a very short message announcing that it is awake. When bridge 40 receives this signal, it will send a command signal to patch 20. If bridge 40 watches patch 20 to perform an operation, such as reporting its configuration or status or uploading measurements, bridge 40 sends a command to perform this function. If no action by patch 20 is desired at this time, bridge 40 sends a 'sleep' command. Upon receiving a sleep command, patch 20 turns off power to a portion of the electronics including, in this example and referring to FIG. 2C, all power to the transmitter 206, receiver 209, sensor interfaces 212, 214, and 216 which also removes power from sensors 232, 234, and 236. The patch also turns off a portion of the processor 202, which is described in more detail in FIG. 6. Patch 20 remains in this sleep state until the portion of processor 202 that is still on wakes up patch 20 by turning on the rest of the processor and the other electronics that have been turned off. The time of this sleep state is selected such that patch 20 wakes up at the beginning of the next time slot.

Figure 6:
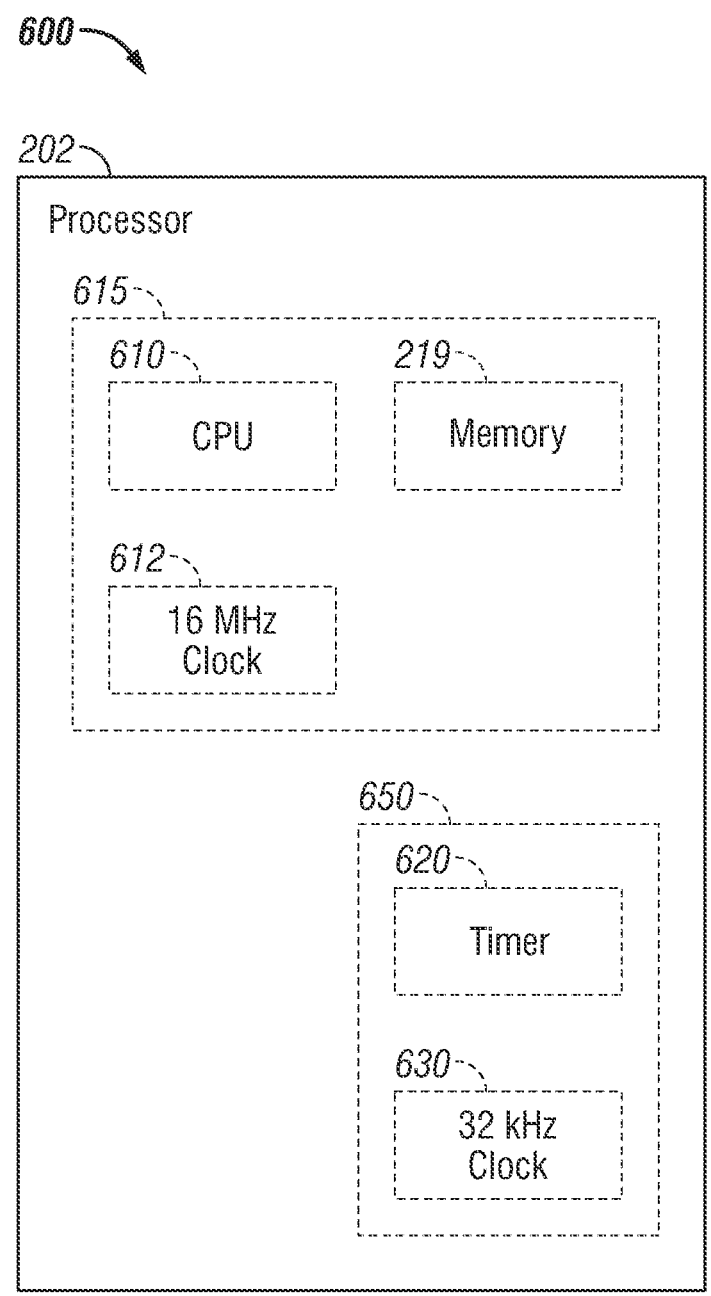
FIG. 6 is a functional block diagram illustrating exemplary details of the processor of FIG. 2C according to certain aspects of the present disclosure.

Referring to FIG. 6, processor 202 may have more than one section of circuitry that can be independently operated. In this example, there is a high-power section 615, which contains the CPU 610 and memory 219 and is driven by a 16 MHz crystal clock 612, and a low-power section 650, which contains a timer 620 which is driven by a 32 kHz crystal clock 630. Section 615 can be turned off by CPU 610. Crystal clocks consume more power relative than other types of semiconductor devices, and the amount of power consumed by a crystal clock is proportional to the frequency of the crystal, as a fixed amount of electrical charge is consumed to switch states at every oscillation. A 16 MHz crystal will usually consume much more power than a 32 kHz crystal as the frequency of the crystal is 500 times higher. Section 650, in this example, contains low-power fixed-duration hardware timer 620 and low-power clock 630.

In this example, timer 620 runs continuously and sends out an 'interrupt' signal every 8 seconds. If section 615 is off when the interrupt signal is sent out by timer 620, section 615 turns on and then CPU 610 sends out commands to turn on the rest of the electronic components of patch 20. The state of patch 20 is termed "awake" when both section 615 and section 650 are on and "asleep" when only the low-power section 650 is on. The power consumption while the patch 20 is awake is higher than the power consumption while patch 20 is asleep.

Referring again to FIG. 5, exemplary power levels of the three states of patch 20 are marked on the vertical axis—'asleep', 'awake' during which patch 20 can receive signals, and 'transmit' during which patch 20 is transmitting signals to bridge 40. Initially, patch 20 is asleep and the power consumption level is low. At the beginning of time slot 1 in frame N−2, timer 620 in processor 202 times out and sends out its interrupt, turning on the high-power section 615 of processor 202 and the rest of the circuitry of patch 20. This is shown as event 520. Bridge 40 is synchronized with patch 20 and knows that time slot 1 is assigned to this patch 20. In this example, bridge 40 sends a 'sleep' command to patch 20, patch 20 turns off its high-power section and associated circuitry and the power level drops back to the initial low level. Patch 20 remains asleep until the timer again times out and patch 20 wakes up at event 521. Bridge 40 again sends a 'sleep' command. This repeats, in this example, through events 522 and 523. When patch 20 wakes up at event 524, however, bridge 40 sends a command to upload stored measurement data. This is reflected in the power level of event 524 rising to the 'transmit' level of power consumption. After the data is received, bridge 40 sends a 'sleep' command and patch 20 goes to sleep. When patch 20 wakes up at events 525 and 526, the bridge sends a 'sleep' command.

As timer 620 is running continuously, the interrupt signal that timer 620 ends out remains synchronized with frame sequence 410 independent of how long patch 20 remains awake in each time slot 430.

As can be seen from plot 510, the average power consumption of patch 20 is much lower in this mode of operation that it would be if patch 20 was awake for the entire time. For the example in which the duration of the time that patch 20 is awake during events 520-523 and 525-526 is 0.5 seconds, and the duration of a frame 420 is 8 seconds, and if the power consumption when patch 20 is asleep is 10% of the power consumption while the patch is awake, then the average power consumption of this configuration will be (0.5/8.0)*0.10=0.00625 or approximately 0.6% of the power that would be consumed if patch 20 was awake the entire time. It can be seen that implementation of this mode of operation has the potential to extend the battery life by a factor of more than 100× compared to a similar unit that is continuously awake. This reduced level of average power consumption of this example would enable a battery-powered device to operate for 100× longer that a similar unit that is continuously awake or, alternately, the use of a 100× smaller battery to provide an equivalent operating life to a similar unit that is continuously awake. A smaller battery enables the overall size and weight of patch 20 to be smaller which is less intrusive and more comfortable to the patient 10 who is wearing the patch 20.

It can be seen that the disclosed embodiments of the vital-signs monitor patch provide a mobile solution to monitoring the vital signs of a patient. The design of the vital-signs monitor patch frees nurses, or other caregivers, from the task of repetitively measuring the vital signs of their patients, allowing the caregivers to spend more time on other duties. The ability to continuously monitor a patient's vital signs using a monitor patch, together with the rest of the patient monitoring system, increases the ability of the nurse to respond quickly to a sudden change in a patient's condition, resulting in improved care for the patient.

The reduction of power consumption in the vital-signs monitoring patch enables the patch to be smaller and lighter than it would be if the disclosed features were not utilized. A smaller patch will be more comfortable to wear and less intrusive in normal activities of the patient as well as less expensive to manufacture. Increased comfort by the user and reduced cost to the facility providing the care will result in an increased likelihood that the device will be used, resulting in improved patient safety.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more."

Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The term 'battery' is intended to encompass all energy storage devices which deliver electricity. These energy storage devices may be rechargeable or single-use. This includes but is not limited to batteries using lead-acid, zinc-carbon, alkaline, nickel cadmium, lithium, and lithium-ion technologies, capacitors, generators powered by springs or compressed gas or other mechanical energy storage mechanisms, and fuel cells.

Those of skill in the art will appreciate that the various illustrative functional bocks, modules, components, methods, and algorithms described herein may be implemented as hardware, software, or a combination of the two. Various components and functional elements may be arranged in a different configuration or partitioned in a different way without departing from the scope of the claimed invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vital-signs monitor for a patient monitoring system, comprising:
   a transceiver configured to transmit and receive wireless signals to a healthcare network;
   a sensor interface;
   a patient sensor coupled to the sensor interface, the patient sensor configured to measure a property of the patient;
   an energy storage device;
   a monitor processor connected to the transceiver, the energy storage device, and the sensor interface, wherein:
     the monitor processor comprises first and second sections and a timer that is configured to time out after a specified time period and cause to turn on power from the energy storage device to the first section of the monitor processor, the sensor interface, and the transceiver that have been turned off, and start a new timing period;
     the monitor processor is configured to, upon receipt of a command to upload a stored measurement data, transmit the stored measurement data in a pre-selected time slot assigned to the vital-signs monitor in a frame of a data stream of a bridge device, wherein the timer is synchronized among a plurality of vital-signs monitors in communication with the bridge device so that the pre-selected time slot is one among a plurality of time slots in the frame of the data stream assigned to the plurality of vital-signs monitors by the bridge device; and
     the monitor processor is configured to, upon receipt of a sleep signal, turn off power from the energy storage device to the first section of the monitor processor and turn off power from the energy storage device to the sensor interface and the transceiver, wherein the monitor processor is configured to receive the sleep signal transmitted from the bridge device during the pre-selected time slot,
   wherein the transceiver, the sensor interface, the energy storage device, the patient sensor, and the monitor processor are each affixed within or on a housing formed of at least a first layer attached to a second layer by a moisture and particulate resistant seal,
   wherein the energy storage device is suitable for mobile use on a user-worn device based on power management by the monitor processor,
   wherein the data stream comprises a frame sequence of a plurality of frames, each frame having the same internal structure with the same pre-selected time slot for transmitting a signal to the vital-signs monitor, and
   wherein an interrupt signal sent by the timer remains synchronized with the frame sequence independent of how long the vital-signs monitor remains awake in each pre-selected time slot.

2. The vital-signs monitor of claim 1, wherein the timer is configured to time out after a fixed period of time.

3. The vital-signs monitor of claim 1, wherein the timer is configured to provide the interrupt signal as a periodic interrupt signal that turns the first section of the monitor processor on when the first section of the monitor processor is off.

4. The vital-signs monitor of claim 3, wherein a second section of the monitor processor puts the first section of the monitor processor to sleep at an end of the pre-selected time slot assigned to the vital-signs monitor.

5. The vital-signs monitor of claim 3, further configured so that a rate of power consumption while the first section of the monitor processor is turned off is lower than a rate of power consumption while the monitor processor is turned on.

6. The vital-signs monitor of claim 1, further configured to consume power at a first rate when the transceiver, the sensor interface, and the monitor processor are fully turned on and consume power at a second rate when the transceiver, the sensor interface, and the first section of the monitor processor are turned off, wherein the second rate is lower than the first rate.

7. The vital-signs monitor of claim 1, wherein:
the monitor processor comprises a first clock and a second clock;
the first clock consumes more power than the second clock;
the first section of the monitor processor that is turned off comprises the first clock;
the second section of the monitor processor comprises the second clock; and
the timer is configured to operate from the second clock.

8. The vital-signs monitor of claim 1, wherein the timer is configured to run continuously and automatically start a new timing period when it times out, wherein the new timing period is configured to start at the beginning of the pre-selected time slot of the next frame of the plurality of frames in the data stream of the bridge device.

9. The vital-signs monitor of claim 1, wherein the patient sensor is configured to monitor at least one of an accelerometer, a temperature sensor, or an oxygen saturation sensor.

10. The vital-signs monitor of claim 1, wherein the patient sensor is an external sensor that is operably coupled with the vital-signs monitor via one of a cable or a wireless coupling.

11. The vital-signs monitor of claim 1, wherein the sensor interface comprises an electronic component configured to perform one of generating an excitation signal to a sensor or providing a direct-current (DC) power to a sensor.

12. The vital-signs monitor of claim 1, wherein the sensor interface comprises one of a signal generator for generating an excitation signal to the patient sensor, a voltage regulator for providing power to the patient sensor, an amplifier for amplifying a sensor signal from the patient sensor, an analog-to-digital converter for digitizing an amplified sensor signal, or a filter for filtering out noise from the patient sensor.

13. The vital-signs monitor of claim 1, further comprising a printed circuit board, wherein an internal sensor is mounted on the printed circuit board and is configured to measure a temperature of the printed circuit board.

14. The vital-signs monitor of claim 1, wherein the monitoring processor is configured to send configuration information to an external device through the transceiver.

* * * * *